US007550184B1

(12) United States Patent
Fabritz

(10) Patent No.: US 7,550,184 B1
(45) Date of Patent: Jun. 23, 2009

(54) METHOD OF PROCESSING CACTI SKELETONS AND THE RESULTING ARTICLE

(76) Inventor: Michael Fabritz, 2804 N. Jamison, Flagstaff, AZ (US) 86004

( * ) Notice: Subject to any disclaimer, the term of this patent is extended or adjusted under 35 U.S.C. 154(b) by 774 days.

(21) Appl. No.: 10/832,497

(22) Filed: Apr. 26, 2004

(51) Int. Cl.
*A01N 3/00* (2006.01)
*A01G 5/06* (2006.01)

(52) U.S. Cl. .............................. 428/15; 428/17; 428/22

(58) Field of Classification Search .................. 428/15, 428/17, 22; 434/296, 297; 426/262, 253; 422/32; 436/163, 8, 18, 176; 427/2.1–4
See application file for complete search history.

(56) References Cited

U.S. PATENT DOCUMENTS 3,861,053 A * 1/1975 Rovetti ......................... 34/353

OTHER PUBLICATIONS

Cactus Lace—Homemade Texas Jams, Jellies and Salsa (www.cactuslace.com) "Cactus Art" 3 Pages, Apr. 26, 2004.

* cited by examiner

*Primary Examiner*—Timothy M Speer
*Assistant Examiner*—Gordon R Baldwin
(74) *Attorney, Agent, or Firm*—John R Daugherty

(57) ABSTRACT

A method for processing prickly pear cactus skeletons and the resulting article. The process produces stabilized, acid and mold-free planer or three-dimensionally formed, cactus skeletons that can be easily handled. The method of the present invention preserves and enhances the natural intricate and delicate vein-like structures of the native skeleton and effectively alters the natural pH to a highly non-acidic state. Prickly pear cactus skeletons processed by the inventive method are ideally suited to be used as, or incorporated into, museum quality frame matting.

13 Claims, 8 Drawing Sheets

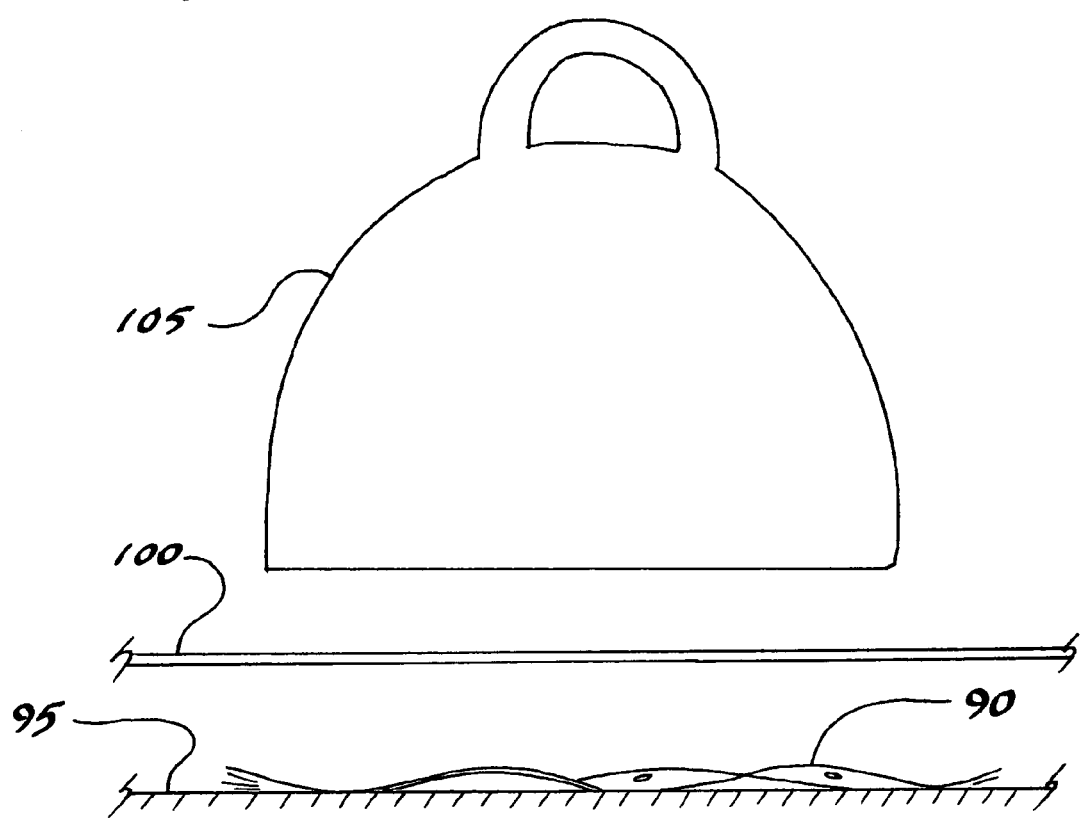

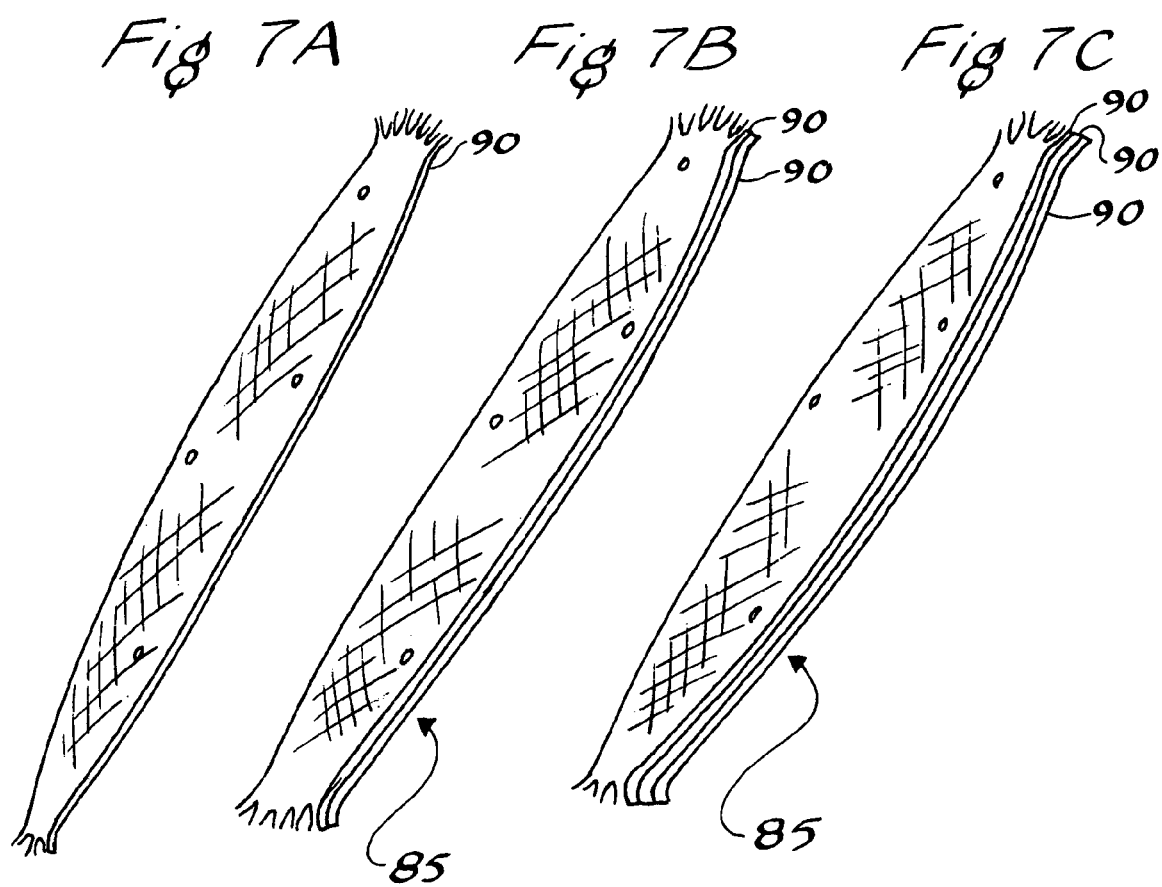

METHOD OF PROCESSING CACTI SKELETONS AND THE RESULTING ARTICLE

FIELD OF THE INVENTION

The invention relates to methods of processing cactus skeletons and more particularly to processed prickly pear cacti skeletons having an altered pH level.

BACKGROUND OF THE INVENTION

There are various cacti native to the United States, Mexico and South America. The particular cacti genus *Opuntia* includes the beaver tail cacti, the bunny ear cacti and other prickly pear cacti. A common prickly pear cactus is generally characterized by a low-lying cluster of oblong shaped pads, protruding at multiple angles having barbed spines or tiny stickers. During the late spring and early summer each pad produces several flowers that bloom in an array of colors depending on the particular variety. When the bloom fades an edible fruit is formed. The pads of a common prickly pear cactus are actually rapidly growing flattened stems. Depending on the variety, the pads will grow from about four to 16 inches long, nine inches wide, and about three-quarters of an inch thick. The pads may be elliptical to oblong in shape, bright green to blue-gray in color and have a generally smooth skin.

The multiple forms of the cacti genus *Opuntia* have been used commercially in a variety of ways. For example the cacti have been used for hedges, natural fences and erosion control, particularly in deforested areas. The sap from the pads can be used as a first aid similar to the aloe vera plant. Ground or pureed young pads are used as a laxative and also as a potential remedy for diabetes. The sap from the pads is used as a mosquito repellent and as a means to smother mosquito larvae. The sap can also be extracted to form chewing gum, candles and can be concentrated and mixed with whitewash/mortar to increase the durability of buildings.

There are numerous culinary uses for the cactus genus *Opuntia*. The fresh pads of the prickly pear cactus provide a dependable source of food and drink for livestock and poultry. The pads are a traditional vegetable in Central Mexico and are eaten raw in salads, boiled and fried like eggplant, pickled with spices or cooked with shellfish, pork, chilies, tomatoes and eggs. The fruit of the prickly pear cactus vary in size and shape and can be cooked into jams, preserves, syrups and candies.

As described above, the majority of uses of the prickly pear are derived from the cactus pads or fruits. A third component of a common prickly pear cactus is an internal woody "skeleton" which is encased in the cactus pad. A typical skeleton is comprised of several layers of an intricate network of woody vein-like structures and has the general shape of the original cactus pad. This "woody skeleton" of the cactus is often considered a "by-product" or waste resulting from a specific method of processing. The skeletons of the prickly pear have had limited use in the construction of houses, and have been formed into rustic furniture and assorted trinkets. Recently entire woody skeletons have been "picture framed" and presented as art. See for example the WebPages www.cactuslace.com, which displays examples of complete or entire prickly pear skeletons mounted as art in picture frames.

When closely examined, the fine detail and intricacies of a prickly pear cactus skeleton present a very intriguing and unique visual experience. The skeleton therefore has potential for use in a variety of ways that utilize the artistic aspects of the skeleton. Most of such "artistic" applications however will require a skeleton that has a consistent form and predictable mechanical properties. Such a cactus skeleton should also permit reasonable handling during construction and shipping. Ideally such a cactus skeleton could be formed into planer or three-dimensional shapes. Also of high importance is the long-term acid/base or "pH" level of the cactus skeleton. To be "Museum Quality" the skeleton must have a uniform, base pH and must not be acidic. Such materials should ideally have a base pH that is in the range of between 8-10. In this base range, the material pH is distanced from being acidic and also provides a "safety margin" in the event of the material changing towards being acidic.

Unfortunately dead cactus skeletons have a pH that is close to acidic, are commonly stained with mold and bacteria and vary widely in shapes and mechanical properties. In addition a complete or entire skeleton is comprised of several entwined skeleton layers and is not substantially planer.

SUMMARY OF THE INVENTION

The present invention is a method for processing prickly pear cactus skeletons and the resulting article. The inventive process produces stabilized, acid and mold-free planer or three-dimensionally formed, single layer skeletons that can be easily handled. The method of the present invention preserves and enhances the natural intricate and delicate vein-like structures of the native skeleton. The method of the present invention can be applied to dead cacti and does not require the harvesting of living cacti. The process of the present invention effectively alters the natural pH of a cactus structure to a highly non-acidic state. In a preferred embodiment, prickly pear skeletons processed by the inventive method are used as, or incorporated into, museum quality frame matting.

BRIEF DESCRIPTION OF DRAWINGS

Shown in FIG. 1 is an isometric view of a prickly pear cactus skeleton that has been processed according to the present invention. The skeleton has a generally rectangular shape.

Shown in FIGS. 2A through 2C are front plane views of three examples of picture frames incorporating various configurations of matting of the present invention.

Figure 3:
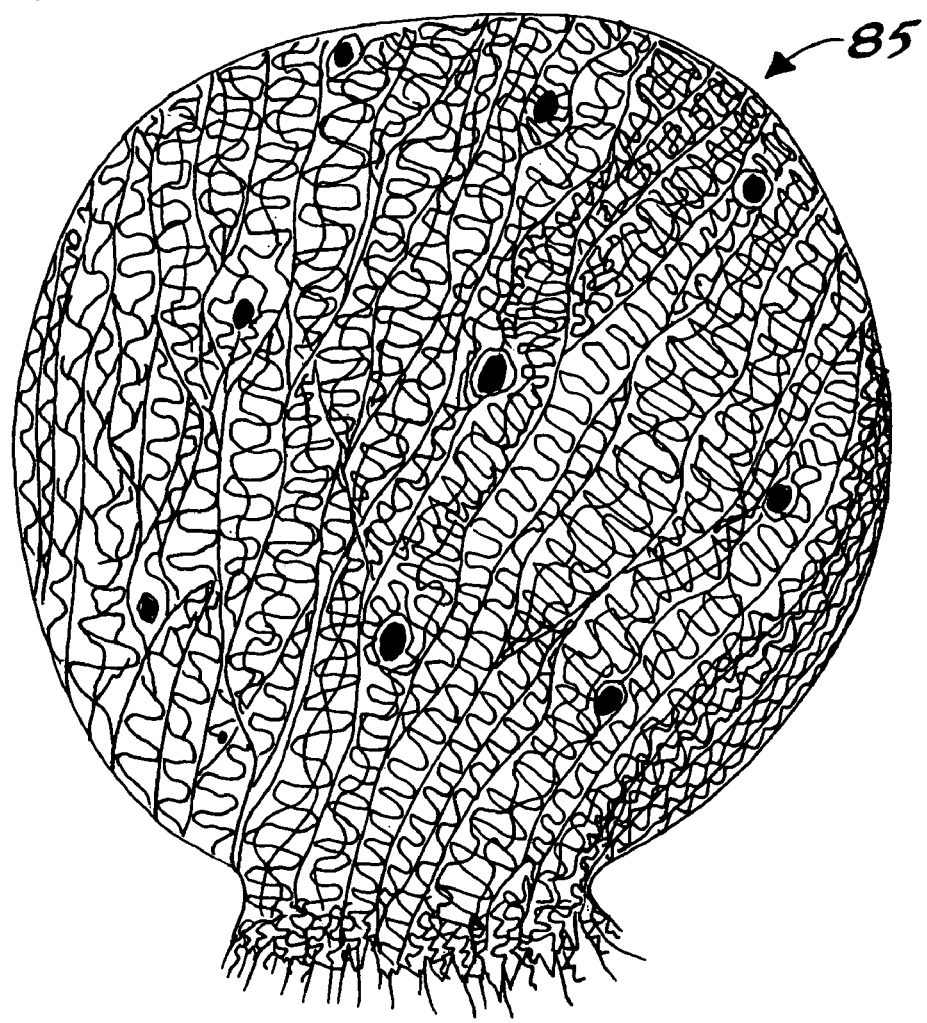

Shown in FIG. 3 is a front plane view of a typical group of skeletons after pad removal according to a process of the present invention. The group of skeletons is comprised of several individual skeletons layered in a laminate form.

Figure 4:
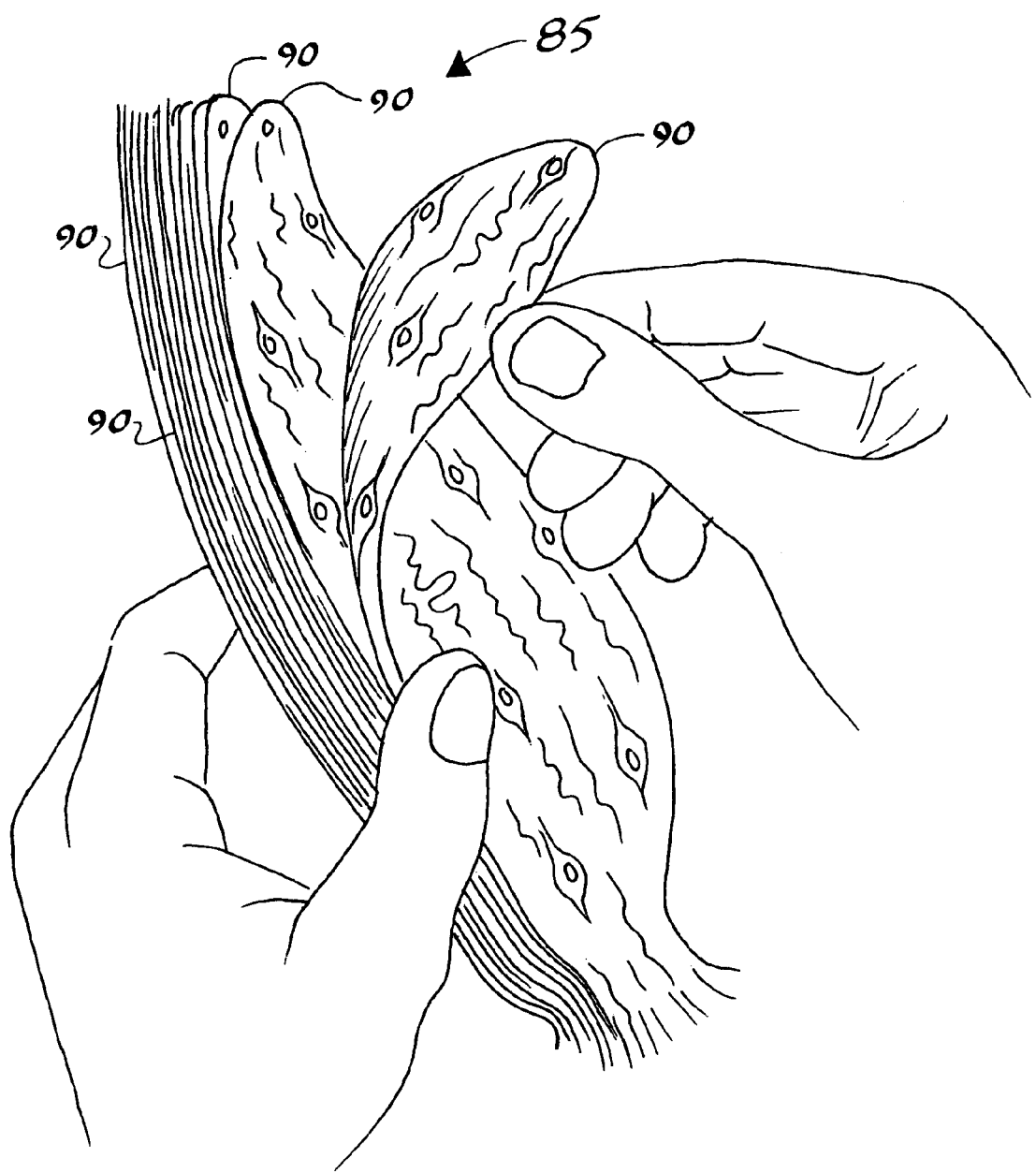

Shown in FIG. 4 is an isometric view of a group of skeletons comprised of several individual skeletons layered together in a laminate form.

Shown in FIG. 5 is a front side view of an individual skeleton positioned onto a hard flat surface according to a process of the present invention. The skeleton is also shown covered with a layer of dry cardboard with a suitable weight placed onto the cardboard to compress the skeletons.

Figures 6A, 6B:
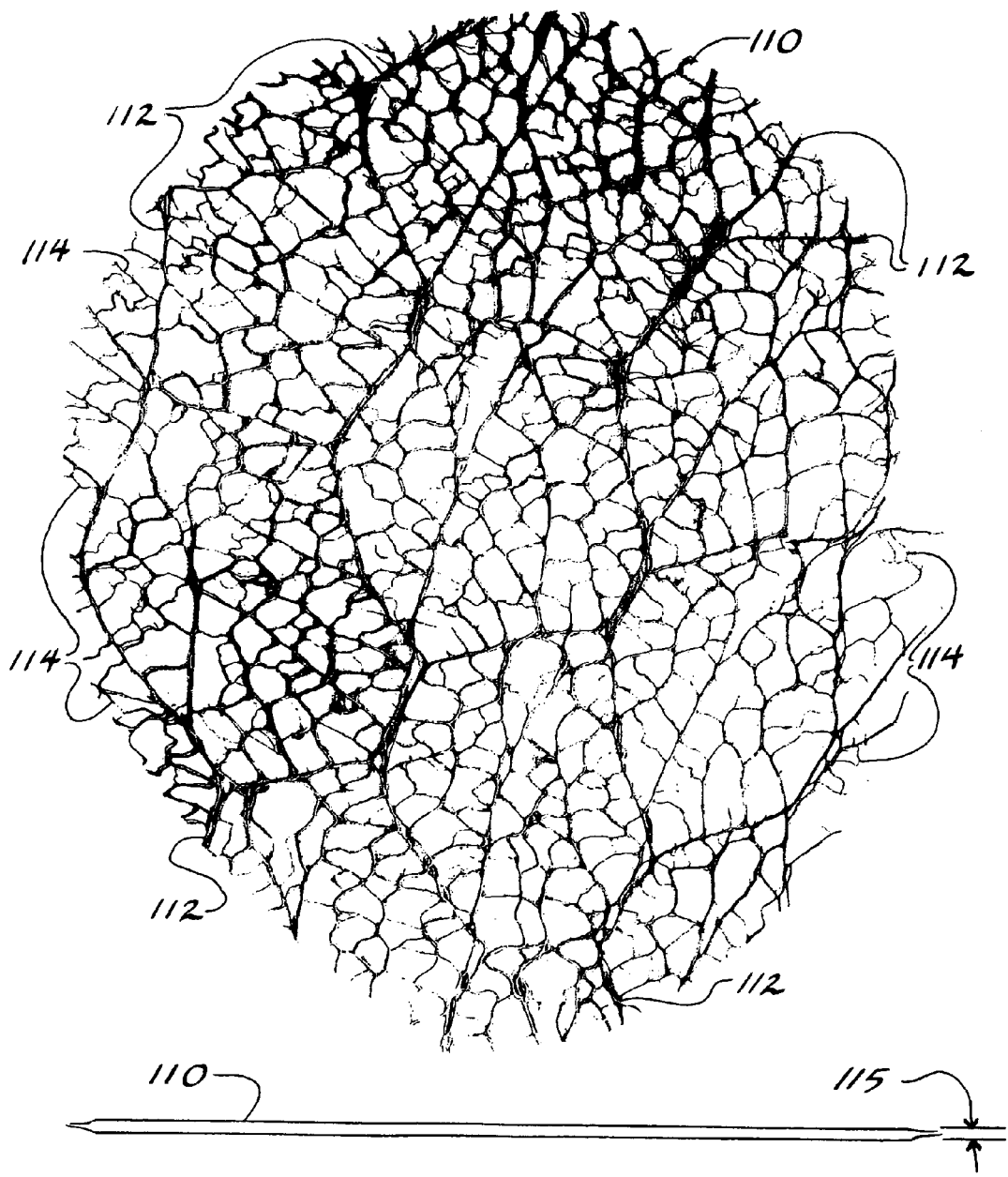

Shown in FIG. 6A is a top plane view of a typical prickly pear cactus skeleton after being cleaned, pressed and dried according to the present invention. Shown are numerous veins and interconnected cross-fibers of the skeleton.

Shown in FIG. 6B is an edge side view of a typical prickly pear cactus skeleton after being cleaned, pressed and dried according to the present invention.

Shown in FIGS. 7A through 7C are examples of skeleton lamination configurations. Shown in FIG. 7A is single skeleton compared to FIGS. 7B and 7C that show respectively two skeletons laminated together and three skeletons laminated together.

Figure 8A:
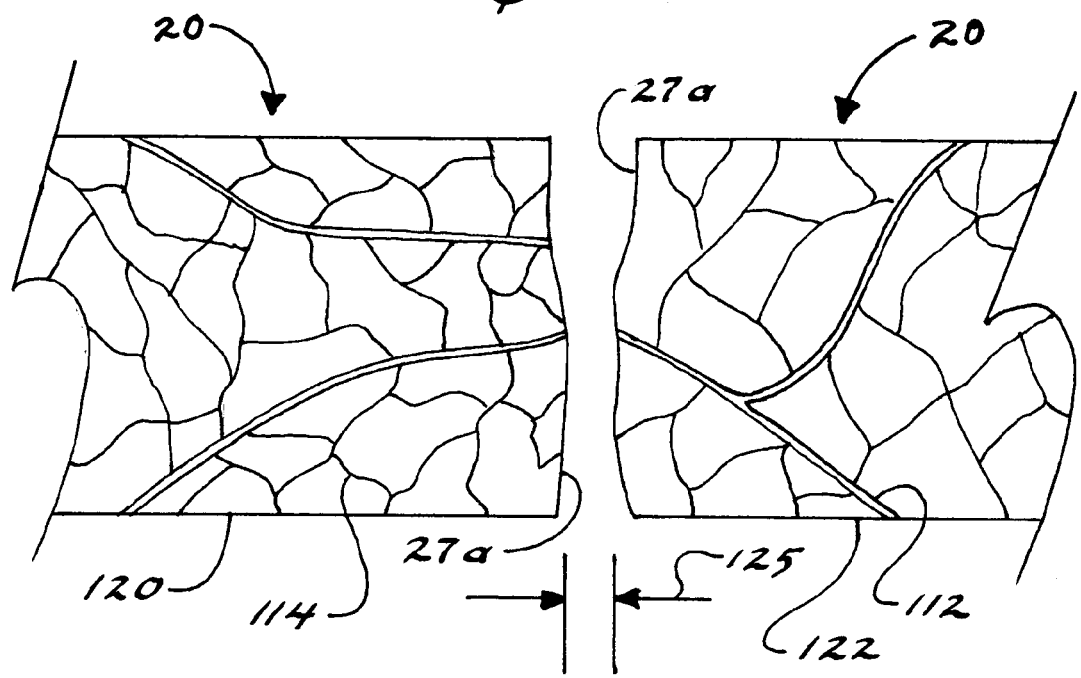
Figure 8B:
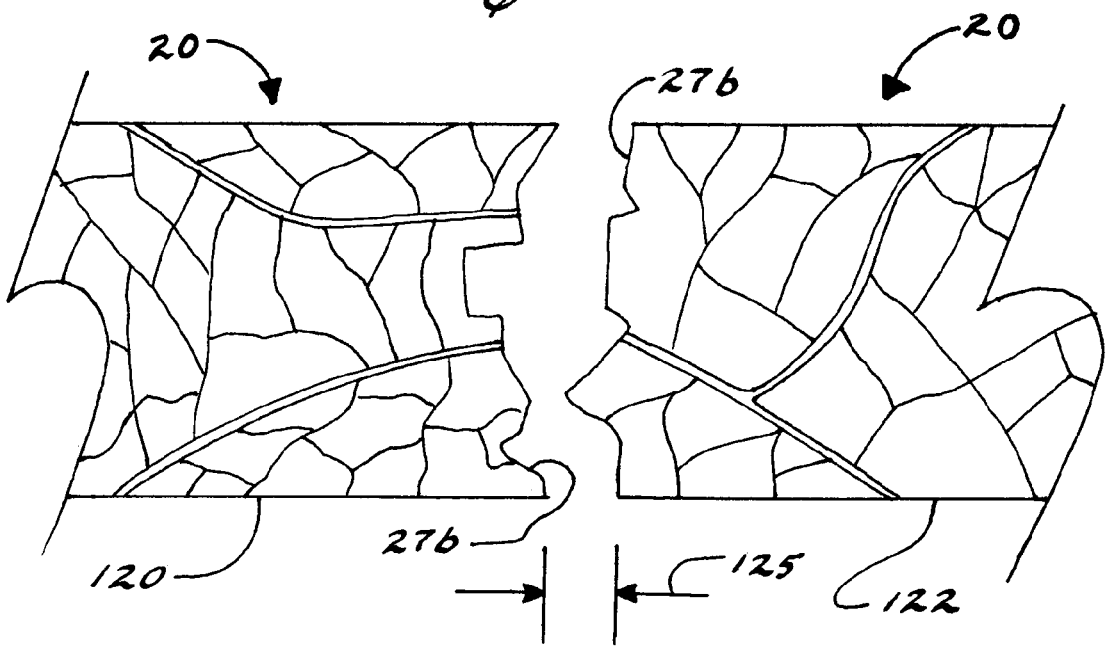

Shown in FIGS. 8A and 8B are partial top views of two processed cacti skeletons having cut edges that are aligned and positioned together to form a structure that is larger than a single cactus skeleton. FIG. 8A depicts an essentially linear cut line while FIG. 8B shows an essentially non-linear cut line.

DETAILED DESCRIPTION OF DRAWINGS

Figure 1:
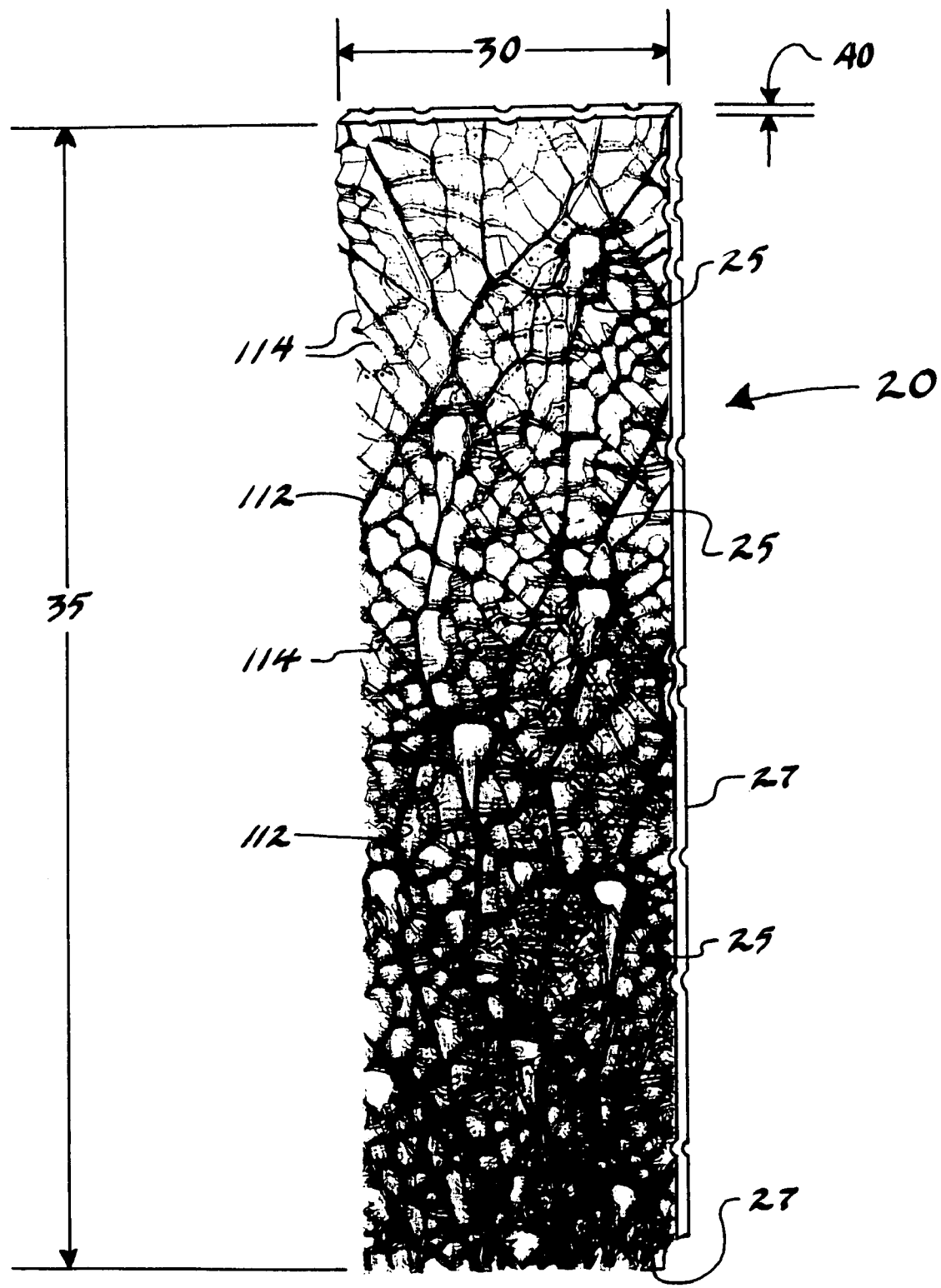

The method and resulting article of the present invention is ideally suited for use as picture matting. Shown in FIG. 1 is an isometric view of a prickly pear cactus skeleton 20 that has been processed according to the present invention. Shown is a rectangular-shaped processed cactus skeleton 20 comprised of woody vein-like elements 25. The skeleton can be described as having a series of "veins" 112 with interconnected "cross-fibers" 114. In general the veins 112 are larger than the cross-fibers 114 and are also longer in length than a typical cross-fiber. The processed cactus skeleton has a width 30, a length 35 and a thickness 40. The cactus skeleton processed according to the present invention can be cut to dimensions typically suited for picture frame matting. Shown in FIG. 1 are four cut edges 27 of a processed skeleton of the present invention. The cut article 20 can have, for example, a width of about 0.25", about 0.5", about 0.75", about 1", about 1.25", about 1.5", about 1.75", about 2", about 2.5", about 3" about 3.5", about 4" or wider depending on the particular cactus used. Similarly, the cut article length 35 can be about 0.5", about 1", about 2", about 3", about 4", about 5", about 6", about 7", about 8" or longer depending on the particular cactus used.

A desired width 30 and length 35 can be constructed by combining multiple processed cactus segments that are cut and abutted together or placed in close proximity to each other. The cactus skeleton 20 processed according to the present invention can have a thickness 40 of about 0.02", about 0.05", about 0.07", about 0.1", about 0.15", about 0.2" about 0.25" or thicker depending on the specific cactus skeleton and processing method used.

Figure 2A:
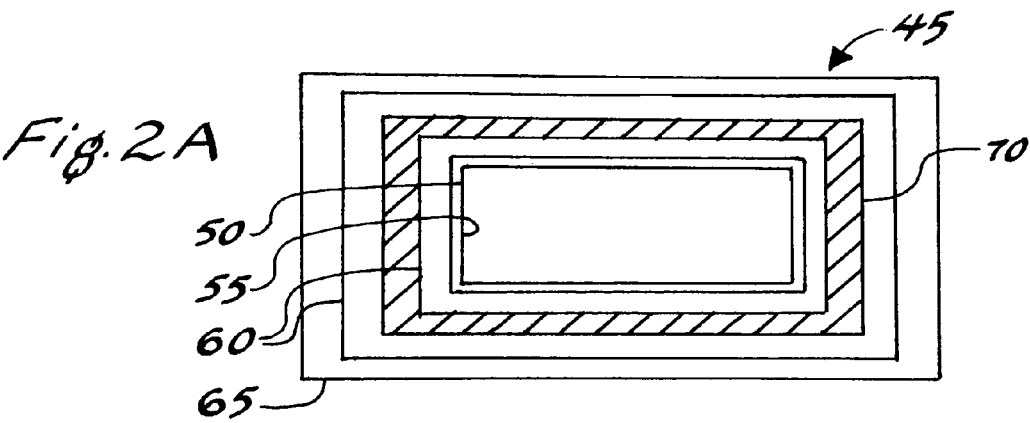
Figure 2B:
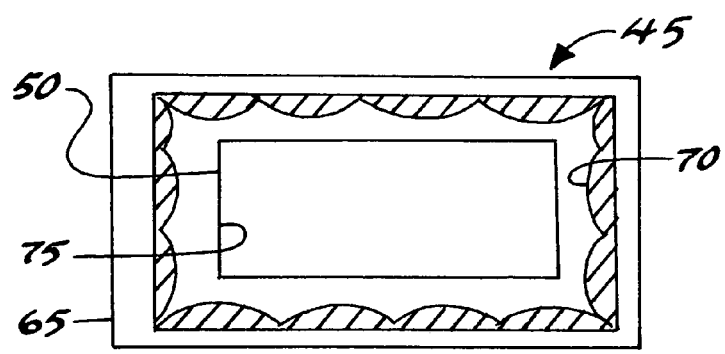
Figure 2C:
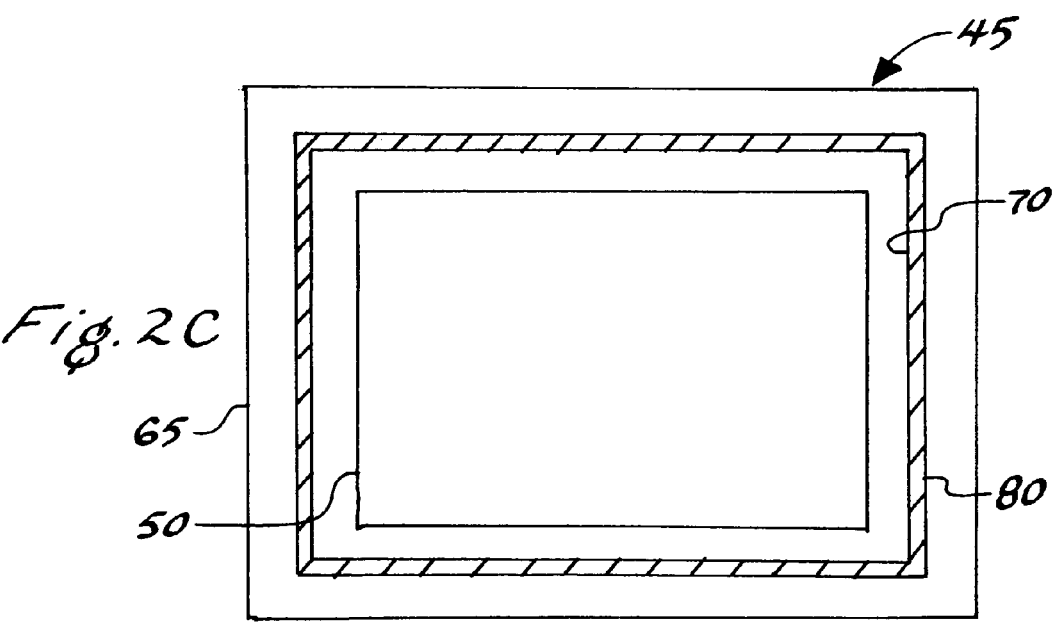

Shown in FIGS. 2A through 2C are examples of picture frames incorporating various configurations of matting of the present invention. Shown in FIG. 2A is a picture frame assembly 45, having a picture 50, a lower mat 55, two upper mats 60 and a frame 65. A matting of cactus skeleton of the present invention 70 is positioned between the two upper mats 60. In this embodiment the cactus skeleton matting 70 has a generally rectangular shape as shown previously in FIG. 1.

Shown in FIG. 2B is a picture frame assembly 45, having a picture 50, a single mat 75 and a frame 65. A matting of cactus skeleton of the present invention 70 is positioned onto the single mat 75. In this embodiment the cactus skeleton matting 70 has a generally scalloped shape.

Shown in FIG. 2C is a picture frame assembly 45, having a picture 50 and a frame 65. The frame 65 is configured with a recess or channel 80 sized to accept a matting of cactus skeleton of the present invention 70 which is "in-laid" into the frame 65. In this embodiment the cactus skeleton matting 70 has a generally rectangular shape as shown previously in FIG. 1.

Shown in FIGS. 2A through 2C are example configurations of cactus skeletons incorporated into a presentation frame. These figures are intended to show example uses of a cactus skeleton processed according to the present invention and are not intended to limit the potential uses.

Prickly pear cacti are of the family Cactaceae and of the genus *Opuntia*. There are about fifteen species inhabiting North American deserts. Larger plant species are more easily handled, yield more skeletons and are in general more suited for processing according to the present invention. Examples of the larger prickly pear cactus species include the Blind Prickly Pear (*Opuntia rufida*); Englemann's Prickly Pear (*Opuntia engelmannii*); the Pancake Prickly Pear (*Opuntia clorotica*); the Santa Rita Prickly Pear (*Opuntia violacea*) and the Texas Prickly Pear (*Opuntia lindheimeri*). The Englemann's Prickly Pear is a preferred species for processing according to the present invention since this particular species has very large pads that can grow to twelve inches in diameter or larger.

As used herein, the term "processed" includes those treatments that expose a cactus skeleton to any of the following: a germicide; a disinfectant; a antiseptic; a high temperature (over 180° F.) liquid or gas; or an operation that removes mold and/or bacteria. The presence of mold or bacteria growth can be determined by visually examining the cactus skeleton under a 3×-magnification aid. To be "devoid" of mold or bacteria, no presence of mold or bacteria will be visually detected under a 3× magnification.

A preferred processing method of the present invention is outlined below:

1) Obtain a suitable prickly pear cactus pad. Dead pads with minimal amounts of decay and damage are preferred.

2) Soak the pad in about two gallons of clean water with about one drop of concentrated Lysol® and one cup of powdered borax. The soak kills bacteria and mold and also helps preserve the wood of the skeleton. The use of warm to hot water, approximately 120° F. to 150° F. aids in the subsequent de-lamination of the skeleton layers. Warm to hot water also expands the wood cells and aids in the penetration of the disinfectant/preservative.

3) Separate the skeleton from the pad material and manually de-laminate the multiple layers of the skeleton. Shown in FIG. 3 is a front plane view of a typical group of skeletons 85 after pad removal. The group of skeletons 85 is comprised of several individual skeletons layered in a laminate form. Shown in FIG. 4 is an isometric view of a group of skeletons 85 comprised of several individual skeletons 90 layered together in a laminate form.

4) Gently scrub the skeletons with dishwashing liquid soap and rinse in clean water to remove any remaining dirt of bio-matter.

5) Soak the cleaned skeletons in about two gallons of clean water (approximately 65-85° F.) with about one drop of concentrated Lysol®, one cup of powdered borax and about one teaspoon of chlorine bleach for one to two hours.

6) Spread out the skeleton layers and place onto a clean, hard flat surface. Cover the skeletons with a layer of dry cardboard. Place suitable weights onto the cardboard to compress the skeletons. A pressure of about 0.05 to 0.1 psi can be used to compress the skeletons. Shown in FIG. 5 is a front side view of an individual skeleton 90 positioned onto a hard flat surface 95. The skeleton 90 is covered with a layer of dry cardboard 100. A suitable weight 105 is placed onto the cardboard to compress the skeletons. Place the skeletons in a well-ventilated area and let air dry for about 48 hours.

7) Remove the weights and separate the skeletons from the cardboard. Shown in FIG. 6A is a top plane view of a typical prickly pear cactus skeleton 110 after being cleaned, pressed and dried according to the present invention. Shown are numerous veins 112 and interconnected cross-fibers 114 Shown in FIG. 6B is an edge side view of a typical prickly pear cactus skeleton 110 after being cleaned, pressed and dried according to the present invention. As shown the processed cactus skeleton has a thickness 115.

8) Using a sharp knife or razor cut and trim the completed skeletons to a desired shape.

9) Apply one or more coats of spray lacquer to preserve and seal the dried skeletons.

There are several alternate preferred processes for forming cactus skeletons according to the present invention. In an alternate process the soak operation of step 5) is eliminated and the hand scrubbed skeletons are directly pressed as in step 6). In addition about one teaspoon of chlorine bleach may be optionally added to the water mixture of the initial soak described in process step 2). The addition of the chlorine bleach may be optionally eliminated in process step 5). Examples of alternate processes may be summarized by the following combinations of the process steps listed above: Alternate process #1 includes steps 1), 2), 3), 4), 6), 7), 8) and 9); Alternate process #2 includes steps 1), 2) with the addition of chlorine bleach, 3), 4), 6), 7), 8) and 9); Alternate process #3 includes steps 1), 2), 3), 4), 5) without bleach, 6), 7), 8) and 9).

Other alternative processes include the pressing or drying of the skeletons into irregular or three-dimensionally profiled shapes. For example the treated skeletons of step 5 above can be pressed onto a three-dimensional shape such as a sphere or a concave surface to impart a non-planer shape. The treated skeletons of step 5 above can also be rolled into tubular shapes, folded or formed into a variety of configurations. Multiple skeletons can also be processed according to the present invention. For example in the delamination process step 3 above, the group of skeletons can be separated into laminated layers having two, three, four, five, six or more individual skeletons. Shown in FIGS. 7A through 7C are examples of skeleton lamination configurations. Shown in FIG. 7A is single skeleton 90 compared to FIGS. 7B and 7C that show respectively two skeletons 90 laminated together and three skeletons 90 laminated together.

Shown in FIGS. 8A and 8B are partial top views of two processed cacti skeletons having cut edges that are aligned and positioned together to form a structure that is larger than a single cactus skeleton. Shown in FIG. 8A are two processed skeletons 20 of the present invention. Each of the two skeletons have a series of woody veins 112 with interconnected cross-fibers 114 and a cut edge 27a that transverses through at least one vein and at least one fiber. The cut edge 27a of the first cactus skeleton 120 is shown aligned and positioned to a cut edge 27a of the second cactus skeleton 122 within a distance 125. Typical distances between cut edges of two or more skeletons of the present invention range from about 0.001" to about 0.1" or more. Shown in FIG. 8A is a cut edge 27a that has an essentially linear shape. An essentially linear shape has the visual appearance of a straight line or that of a line with a maximum deviation from a straight line of less than about 0.1". As shown in FIG. 8A, the first and second cut edges 27a have an essentially linear shape and the first cut edge of the first woody skeleton is aligned and positioned within about 0.1" of the second cut edge of the second woody skeleton. Cut edges of cacti skeletons of the present invention can be positioned and aligned together so that there is no gap between the edges or be positioned and aligned together so that there is an overlap between the edges.

Similarly shown in FIG. 8B is a cut edge 27a that has an essentially non-linear shape. An essentially non-linear shape has the visual appearance of a jagged, stepped, curved or non-linear line or that of a line with a maximum deviation from a straight line of more than about 0.1". Non-linear shapes include but are not limited to interlocking, puzzle-like or other random shapes. Two or more cactus skeletons of the present invention can also be abutted together or separated about a cut line defined by individual cut veins or cross-fibers. Such a join or positioning is considered to incorporate first and second cut edges that have an essentially non-linear shape. As shown in FIG. 8B, the first and second cut edges 27a have an essentially non-linear shape and the first cut edge of the first woody skeleton 120 is aligned and positioned 125 within about 0.1" of the second cut edge of the second woody skeleton 122.

EXAMPLE #1

Several pads of a dead, slightly decayed prickly pear cactus were collected in the central part of Coconino County, near Flagstaff, Ariz. Approximately 1 pound of selected cactus pads were processed as follows: 1) The pads were soaked in about two gallons of clean water with about one drop of concentrated Lysol® and one cup of powdered borax. Warm to hot water, approximately 120° F. to 150° F. was used. 2) The skeletons from the pad material were manually de-laminated into multiple skeleton layers. 3) The skeletons were gently scrubbed with dishwashing liquid soap and rinsed in clean water to remove any remaining dirt of bio-matter. 4) The cleaned skeletons were then soaked in about two gallons of clean water (approximately 65-85° F.) with about one drop of concentrated Lysol®, one cup of powdered borax and about one teaspoon of chlorine bleach for one to two hours. 5) The skeleton layers were then placed onto a clean, hard flat surface. The skeletons were covered with a layer of dry cardboard. Suitable weights were placed onto the cardboard to compress the skeletons. A pressure of about 0.07 psi was used to compress the skeletons. The skeletons were placed in a well-ventilated area and allowed to air dry for about 48 hours. 6) The weights were removed and the skeletons were removed from the cardboard. 7) A sharp razor was used to cut and trim the completed skeletons into rectangular shapes of about 1 to 2 inches wide by about 6 to 9 inches long as depicted in FIG. 1.

EXAMPLE #2

Several pads of a dead, slightly decayed prickly pear cactus were collected in the central part of Coconino County, near Flagstaff, Ariz. Approximately 1 pound of selected cactus pads were processed according to Example #1 with the following exceptions: The one-teaspoon of chlorine bleach was eliminated from process step 4).

EXAMPLE #3

Several pads of a dead, slightly decayed prickly pear cactus were collected in the central part of Coconino County, near Flagstaff, Ariz. Approximately 1 pound of selected cactus pads were processed according to Example #1 with the following exceptions: The chlorine bleach was eliminated from process step 4); the one-cup of powdered borax was eliminated from steps 1) and 4).

EXAMPLE #4

To evaluate inherent and processed pH levels, skeletons processed according to Examples #1, #2 and #3 were individually ground into fine particulate samples, taking care not to contaminate the cactus material. An un-processed prickly pear pad collected in Example #1 was also ground into a fine particulate to be used as a control sample. The particulate samples were placed into clean sample jars and mixed with distilled water, in a ratio of about 10 parts per volume of water to about one part per volume of particulate. The pH level of the four samples was then determined. An Orion pH Meter, Model 720A was initially calibrated using Orion application buffer solutions. Buffer solutions of 4.01, 7.00 and 10.01 were used to perform a three point calibration of the pH instrument. The four cactus samples were then analyzed to determine a pH level.

The untreated cactus pad sample had a pH of about 7.16 which is very close to being acidic and would be considered undesirable for long term usage as a museum quality frame matting.

The sample processed according to Example #1 had a pH of about 9.34 which is ideally "centered" within the desired range of 8 to 10.

The sample processed according to Example #2 had a pH of about 9.25 that is also well positioned within the desired range of 8 to 10.

The sample processed according to Example #3 had a pH of about 8.06 which is within the desired range of 8 to 10 but close to the desired lower limit.

Although the invention has been described in conjunction with specific embodiments, it is evident that many alterations and variations will be apparent to those skilled in the art in light of the foregoing descriptions and annexed drawings. Accordingly, the invention is intended to embrace all of the alternatives and variations that fall within the spirit and scope of the appended claims.

I claim:

1. An artistic material, comprising:
   a woody skeleton of a genus *Opuntia* prickly pear cactus;
   the woody skeleton being visually devoid of mold and bacteria growth when examined under a 3× magnification aid; and
   the skeleton having a pH ranging from about 7.5 to about 9; and
   the pH determined by analysis of a fine particulate sample of the skeleton.

2. The artistic material of claim 1 further comprising:
   the woody skeleton having a plurality of interconnected veins and fibers;
   the woody skeleton having a length, width and at least one cut edge; and
   the cut edge transversing through at least one vein and at least one fiber.

3. The artistic material of claim 1 wherein the skeleton has a pH ranging from about 8 to about 9.

4. The artistic material of claim 2 wherein the cut edge has an essentially linear shape.

5. The artistic material of claim 2 wherein the cut edge has an essentially non-linear shape.

6. The artistic material of claim 1 wherein the woody skeleton is a single layer woody skeleton.

7. The artistic material of claim 1 wherein the woody skeleton is a multi-layer woody skeleton.

8. An artistic material, comprising:
   a first and second woody skeleton of a genus *Opuntia* prickly pear cactus;
   the first and second woody skeleton each having a plurality of interconnected veins and fibers;
   the first woody skeleton having a length, width and at least one first cut edge;
   the first cut edge transversing through at least one vein and at least one fiber of the first woody skeleton;
   the second woody skeleton having a length, width and at least one second cut edge;
   the second cut edge transversing through at least one vein and at least one fiber of the second woody skeleton;
   the first cut edge of the first woody skeleton being aligned and positioned within about 0.1" of the second cut edge of the second woody skeleton;
   the first and second woody skeletons forming at least a portion of a picture frame matting; the first and second woody skeletons are visually devoid of mold and bacteria growth when examined under a 3× magnification aid;
   the skeleton has a pH ranging from about 7 to about 9; and
   the pH determined by analysis of a fine particulate sample of the skeleton.

9. The artistic material of claim 8 wherein the first and second cut edges have an essentially linear shape.

10. The artistic material of claim 8 wherein the first and second cut edges have an essentially non-linear shape.

11. The artistic material of claim 8 wherein the woody skeleton is a single layer woody skeleton.

12. The artistic material of claim 8 wherein the woody skeleton is a multi-layer woody skeleton.

13. An artistic material, comprising:
   a processed woody skeleton of a genus *Opuntia* prickly pear cactus;
   the woody skeleton being visually devoid of mold and bacteria growth when examined under a 3× magnification aid;
   the skeleton having a pH ranging from about 7 to about 9;
   the pH determined by analysis of a fine particulate sample of the skeleton;
   the woody skeleton having a plurality of interconnected veins and fibers;
   the woody skeleton having a length, width and at least one cut edge;
   the cut edge transversing through at least one vein and at least one fiber; and
   the woody skeleton is a multi-layer woody skeleton.

* * * * *